United States Patent

Johnson

Patent Number: 5,627,310
Date of Patent: May 6, 1997

[54] SENSOR ARRANGEMENT FOR ICE BANK CONTROL

[75] Inventor: Martin Johnson, Kenilworth, England

[73] Assignee: IMI Cornelius, Inc., Anoka, Minn.

[21] Appl. No.: 546,002

[22] Filed: Oct. 20, 1995

[51] Int. Cl.$^6$ .................................................. G01N 29/00
[52] U.S. Cl. .................. 73/64.53; 73/61.75; 73/651; 62/59; 62/138
[58] Field of Search .................. 73/170.26, 61.45, 73/61.49, 61.75, 64.53, 651, 32 A; 340/580, 582; 62/59, 138, 139

[56] References Cited

U.S. PATENT DOCUMENTS

| | | | |
|---|---|---|---|
| 2,973,639 | 3/1961 | Banks | 73/32 A |
| 3,706,981 | 12/1972 | Hart | 340/244 R |
| 3,977,242 | 8/1976 | Brown | 73/651 |
| 4,176,524 | 12/1979 | Kamiyama et al. | 62/140 |
| 4,246,795 | 1/1981 | Sig et al. | 73/651 |
| 4,379,244 | 4/1983 | Dinger | 310/312 |
| 4,441,363 | 4/1984 | Hill et al. | 73/170.26 |
| 4,568,922 | 2/1986 | Schwippert et al. | 340/582 |
| 4,823,556 | 4/1989 | Chesnut | 62/139 |
| 4,840,033 | 6/1989 | Garland | 62/59 |
| 4,843,830 | 7/1989 | Haul | 62/59 |
| 4,859,817 | 8/1989 | Cassani | 200/61.41 |
| 4,891,628 | 1/1990 | Zuckerman | 340/582 |
| 4,939,908 | 7/1990 | Ewing et al. | 62/139 |
| 5,022,233 | 6/1991 | Kirshner et al. | 62/138 |
| 5,163,298 | 11/1992 | Hassell et al. | 62/59 |

FOREIGN PATENT DOCUMENTS

| | | |
|---|---|---|
| 0191436 | 8/1986 | European Pat. Off. . |
| 1013182 | 12/1965 | United Kingdom . |
| 1197565 | 7/1970 | United Kingdom . |
| 2078955 | 1/1982 | United Kingdom . |
| 2184821 | 7/1987 | United Kingdom . |
| 2202944 | 10/1988 | United Kingdom . |

Primary Examiner—Hezron E. Williams
Assistant Examiner—Jay L. Politzer
Attorney, Agent, or Firm—Sten Erik Hakanson

[57] ABSTRACT

A sensor arrangement principally for ice bank control using a single probe (9) allowed to resonate at its natural resonant frequency. That resonant frequency is different when ice has adhered to the probe and this is detected to indicate ice growth in the ice bank. A resonator/detector (11) oscillates the probe for short periods of time at regular intervals, which allows ice to form about the probe when not in oscillation.

6 Claims, 2 Drawing Sheets

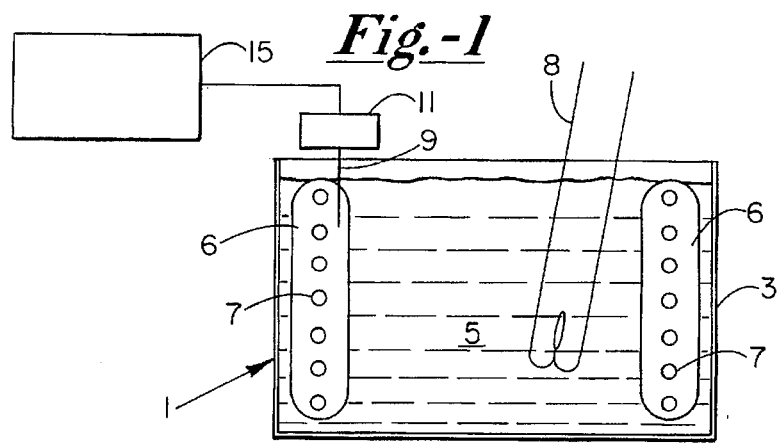
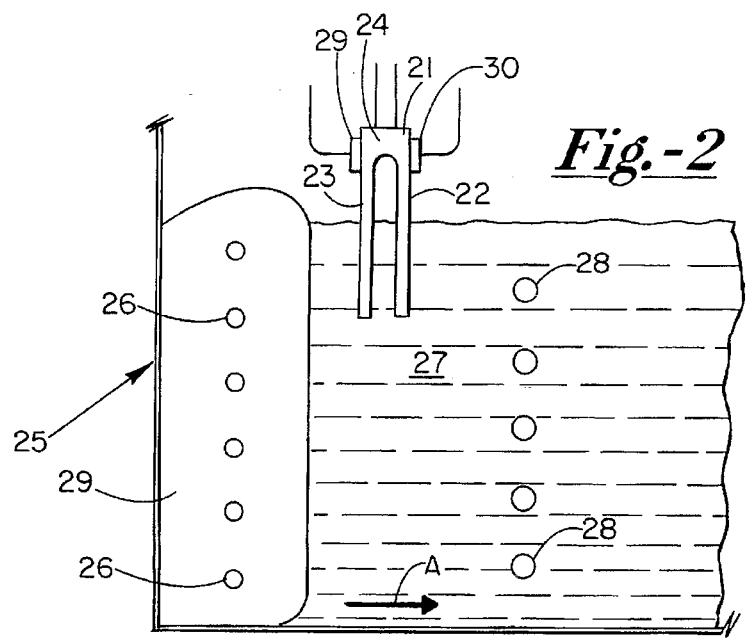
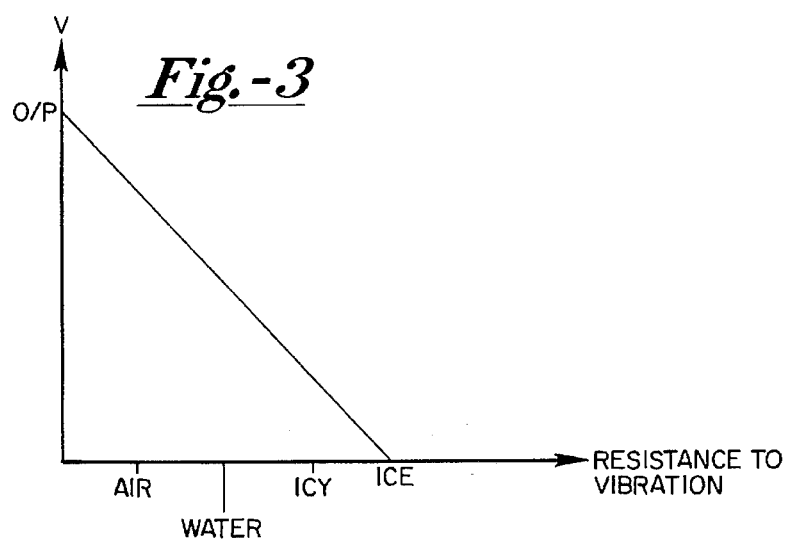

10

5,627,310

1

SENSOR ARRANGEMENT FOR ICE BANK CONTROL

FIELD OF THE INVENTION

The present invention relates generally to a sensor arrangement, and more particularly, but not exclusively, to a sensor arrangement for an ice bank of a beverage dispense system.

BACKGROUND OF THE INVENTION

There is a requirement to sense or detect the level of solid or particulate matter such as grain or rice in a holding vessel. With ice banks of a beverage dispense system it is the thickness or weight of ice formed that requires measurement. Previously, ice in an ice bank has been detected by one of three methods. A first method uses a temperature operated switch arranged to detect the water temperature in the ice bank which is indicative of the ice formed. This temperature approach suffers from inherent inaccuracy and a wide differential in performance of switches. Furthermore, location and maintenance of the switch is essential to achieve reasonable results.

A second approach is to employ a mechanical switch which is effectively displaced as the ice grows within the ice bank. Again, the problems of inconsistency are present, and in addition, it is important to ensure the mechanical switch has an actuator that is displaced by the surface of the ice and does not become enveloped within the ice.

A third method involves the use of two electrical probes. An electrical current is passed between the probes and the conductance is drastically altered as ice is formed there between. Obviously, this method has problems of electrolysis of the probes along with disposition of dirt and dissolved salts thereon. Furthermore, this method is affected by the electrolyte content of the supplied water, so each system must be initially set up by experienced personnel.

Accordingly, it would be highly desirable to have an ice bank sensing system that is reliable, accurate, an not generally affected by water electrolyte levels.

SUMMARY OF THE INVENTION

In accordance with the invention there is provided a sensor arrangement comprising a probe arranged to resonate and detector means arranged to detect changes in the probe resonant frequency. The probe is arranged in a vessel such that alteration in the contents of the vessel will alter the probe resonant frequency or amplitude detected by the detector means. Preferably, the vessel is a water bath tank holding a volume of water wherein an evaporator coil of a refrigeration system is submerged therein so that a volume of ice can form on the evaporator.

The probe may be in a vertical, horizontal or inclined attitude. The sensor arrangement is preferably part of a control system to control the level of particulate matter in the vessel, or in the specific case of a beverage dispenser, control the growth of the deposition of ice on the evaporator coil. Thus, it will be appreciated by those of skill that the control system can be used to ultimately control the operation of a mechanism that regulates the entry into the vessel of the particulate matter, or, in the case of an ice bank, the refrigeration system that cools the evaporator.

DESCRIPTION OF THE DRAWINGS

A further understanding of the structure, operation and advantages of the present invention can be had by reference to the following detailed description, which refers to the following figures, wherein:

FIG. 1 is a schematic illustration of an ice probe system configuration.

FIG. 2 is an enlarged schematic illustration of the ice probe in an ice bank vessel.

FIG. 3 is a graphical representation of typical ice probe response within various environments.

DETAILED DESCRIPTION OF THE PREFERRED EMBODIMENT

Figure 4:
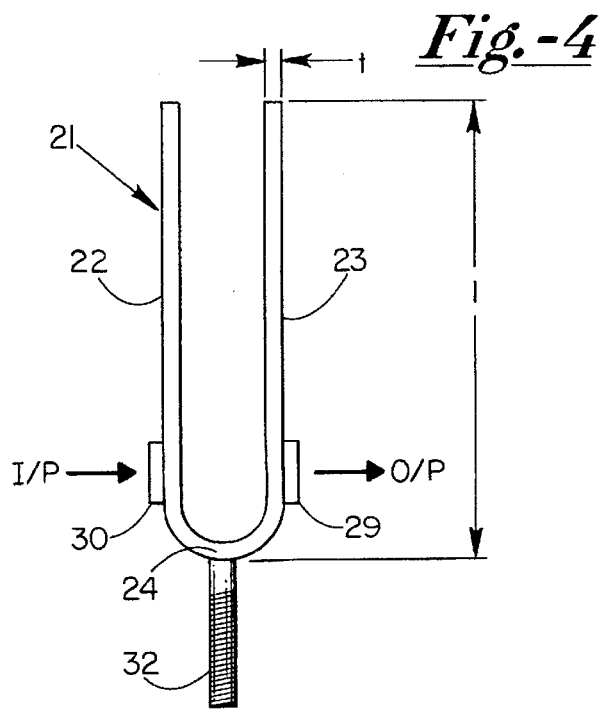
FIG. 4 is a schematic illustration of an ice probe.

Referring to FIG. 1, an ice bank 1 comprises a vessel or vat 3, containing water 5, ice 6 and refrigerator evaporator coils 7. The ice 6 is formed about coils 7 as a blanket. A product coil 8 passes though the bank 1 in order to cool a beverage within before dispense through a dispense tap (not shown). Normally there are several product coils 8 in a bank 1 to accommodate several beverages.

The object of ice 6 is to create an effective cold thermal store during periods of low draw-off through the coils 8 for use during high dispense periods. Thus, it is possible to use a lower rated refrigeration system than would be necessary for peak beverage rates. Evidently, there is an optimum ice thickness, as ice is a relatively poor conductor of heat so creation of ice further from coils 7 becomes less efficient. In order to switch the refrigeration system off it is therefore necessary to detect the optimum thickness of ice. In the present invention, a probe 9 is arranged to extend into bank 1. Probe 9 is typically 50 to 100 millimeters in length, is water proof and located at a spaced position from the coils 7. In operation, probe 9 is oscillated by a resonator/detector 11 at its natural resonant frequency. The resonator 11/probe 9 may be a piezo-electric device. Probe 9 is allowed to oscillate/resonate for short periods at regular intervals so allowing ice to form about probe 9 when it is not oscillating. These off periods ensure that a water pocket is not created about probe 9 due to localised mixing and temperature enhancement due to vibration. The time period between oscillation pulses may be up to 5 minutes but is principally determined by the degree of deposition control required of the ice 6.

It is at the core of the present invention, that the resonant frequency of the probe 9 is altered as ice is deposited. Thus, the resonator/detector 11 is arranged to detect this change in resonance between two latched levels. A first latch level equivalent to an ice free condition and a second latch level determined in order to equate to the desired level of ice 6. Once the second latch level is achieved then a controller 15 is arranged to switch off the refrigeration system. The detector 11 latch level is regularly updated at each oscillator pulse period and the refrigeration system switched ON if the ice 6 level has deteriorated.

Although the probe 9 is illustrated in a vertical position it will be appreciated that other orientations including horizontal and an inclined attitude could be used. The probe 9 could be used to detect the difference between an empty or full grain or rice silo by utilisation of the difference in resonant frequency between the probe 9 in air and when surrounded by grain/rice.

FIG. 2 illustrates an ice probe 21 in greater detail. The probe 21 is made up on an input tine 22 and an output tine 23 separated by an anti-node area 24 of the probe 21. Typically, most of the probe 21 will be submersed in water/ice of a vat 25 which includes evaporator coils 26 of a refrigeration system, a volume of water 27 and product coils 28.

An ice bank 29 is generated about the evaporator coils 26 and grows generally in the direction of arrowhead A. This ice bank 29 as indicated previously acts as a thermal store to accommodate periods of high dispense through the product coils 28. Consequently, the ice bank 29 grows during periods of inactivity or low dispense until it impinges upon the output tine 23 of the probe 21.

The effect of this ice contact is to alter the pick-up frequency of the output tine 23 received from the input tine 22. This alteration in pick-up frequency or amplitude in the output tine 23 is conveniently detected using a piezo-electric crystal 29. Such crystals 29 provide an electrical signal when stressed by deformation. Thus, these electrical signals can be sent to electronic process elements to determine changes in environmental conditions about the tine 23 and so control operation of the ice bank refrigeration system.

It will be understood that the input tine 22 induces oscillation in the pick-up or output fine 23. Conveniently, the input tine 22 is forced to oscillate by a driving piezo-electric crystal 30. Oscillation is achieved by applying an electrical potential across the crystal 30. As an alternative, and in suitable circumstance, it may be possible to use the natural vibration effects in the vat 25 from the refrigeration system compressor and other environmental vibration sources such as agitator elements. Furthermore, independent dedicated vibration sources could be used including bubble generators, etc.

It will be understood the major advantage of using a piezo-electric crystal or dedicated vibration generator is that environmental noise can be more easily eliminated and so the prospect of spurious results reduced. Furthermore, frequencies such as those used in electrical mains (50 HZ) and their multiples should be avoided for similar reasons. In the present invention it is intended to use pulses of vibration at intervals of about 30 seconds. The frequency of the vibrations may be 120 HZ or several KHZ in order to avoid environmental noise impinging upon the system. Obviously, the actual vibration frequency and pulse interval is tailored to individual requirements.

FIG. 3 illustrates a typical output response from tine 23 in comparison with environmental conditions. It will be seen the response is substantially linear. Furthermore, the tine 23 will vibrate in air with a distinct output compared with water. Thus, the probe 21 can be used as a vat 25 out of water detector as well as an ice bank level detector or as a water level control. As the water 27 is chilled and the ice bank 29 develops until it impinges upon the probe 21 the degree of induced vibration in the output line 23 diminishes. Obviously, when the tine 23 is embedded in ice the degree of vibration and thus electrical output is minimal. Normally, the electrical output of a piezo-electric crystal 29 is in the range of mV and a typical output from induced vibration would be 10 mV.

FIG. 4 illustrates in greater detail the ice probe 21 with input line 22 and output line 23. Each tine 22, 23 has a piezo-electric crystal 29, 30 such as $PbZnTiO_3$ attached at its base near the anti-node 24 between the tines 22, 23. Typically, the probe 21 is made of polyacrylate, titanium, invar, aluminium or glass.

The resonant frequency (n) of the ice probe 21 illustrated in FIG. 4 is given by the formula.

$$n = k^2 \frac{(t)}{8\sqrt{12}} (l) \sqrt{\frac{e}{p}}$$

where
k is a constant and=1.1937
t=tine thickness
l=tine length
e=Youngs Modulus
p=density Thus, if the ice probe 21 is formed from invar with a Youngs Modulus of $21 \times 10^{10}$, a density of 8800 $Kg/M^3$, t=1 mm and l=50 mm, then the resonant frequency n=75 HZ. However, this frequency will alter as ice is deposited about the tines 22, 23. Furthermore, input piezo-electric crystal 30 may induce different frequencies in the ice probe. In order to locate the ice probe 21 in the vat 25 a stem 32 is provided such that the orientation and depth of the probe 21 may be adjusted. To enable such adjustment the stem typically has a screw thread.

The ice probe or sensor 21 may be moulded from plastics materials such as polyacrylate for ease of fabrication and to reduce costs.

Figure 5:
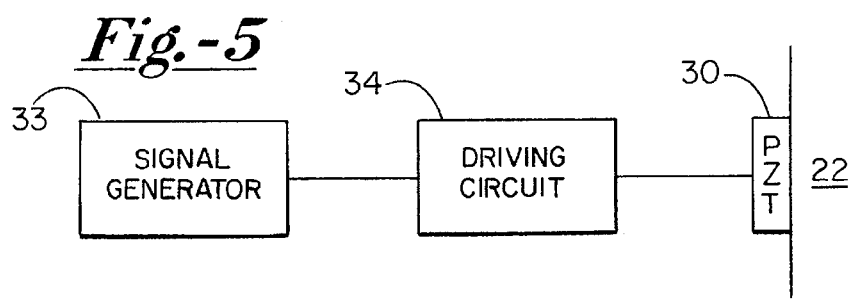
FIG. 5 is a schematic illustration of an input circuitry arrangement for the ice probe.

The drive circuitry for input piezo-electric crystal 30 is shown in schematic form in FIG. 5. The crystal 30 is adhered to the wall of line 22 in some acoustically suitable fashion. A signal generator 33 is arranged to provide pulses or bursts of vibration frequency. Typically, these bursts may be 30 seconds apart and the oscillation or vibration frequency may be 400 HZ. The generator 33 may include two 555 timing circuits suitably coupled to provide the vibration pulses. However, there are a wide range of signal generator systems that could be used.

The vibration pulses are passed to a driving circuit 34. This circuit 34 provides the electrical stimulus for the crystal 30. A convenient driving circuit includes a transformer in which the vibration pulse drives one side and the crystal 30 is coupled to the other side. However, the piezo-electric crystal could be powered in a variety of ways.

The vibration pulses are typically spaced by 30 seconds or so to enable ice to develop about the tines 22, 23.

Figure 6:
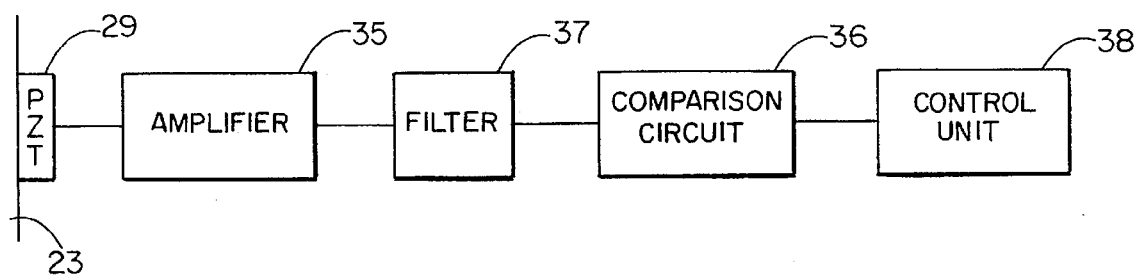
FIG. 6 is a schematic illustration of an output or pick-up circuitry arrangement for the ice probe.

FIG. 6 schematically illustrates the pick-up circuitry coupled to the output or pick-up piezo-electric crystal 29 coupled to tine 23. The electrical signals produced by the crystal 29 are typically in the order of mV. Thus, signals from the crystal 29 are amplified by a factor of 100 or 1000 by an amplifier 35. The signals from the amplifier 35 are electrically filtered in order to remove spurious signals and possibly limit the signals passed to a comparison circuit 36. Thus, the filter 37 may be of the band type or high pass type or loss pass type dependent upon requirements.

The comparison circuit may be a simple comparator in which signals are compared with stored values for air, water and ice and dependent upon the results a controller 37 is stimulated.

The controller 37 may simply switch the refrigeration system of the ice bank apparatus on or off in response to ice probe 21 signals. However, the controller may also give a visual indication of ice probe status, ie. in ice or water. Furthermore, it is advantageous that the controller 37 ensures that several successive ice probe signals are received before determining ice bank status.

It will be understood that several ice probes could be placed at different locations in the vat 25 in order to more accurately determine ice bank growth. Also, the driving circuitry and pick-up circuitry are conveniently time synchronised so that the pick-up circuitry is only operational when the driving circuitry is causing the input tine 22 to vibrate.

It will be understood by a person skilled in the art that vibration amplitude could be detected rather than frequency.

I claim:

1. A sensor control for detecting and regulating the growth of an ice bank in a water bath of a beverage dispensing machine, the ice bank formed on an evaporator of a refrigeration means, the sensor control, comprising:

a probe positioned in the water bath so that ice growth of the ice bank impinges on the probe at a predetermined point, a piezo-electric oscillating means for vibrating the probe at a predetermined source vibrational level, a piezo-electric vibration sensing means for sensing the vibration of the probe, and control means connected to the oscillating means and the vibration sensing means, the control means comparing the sensed vibration of the probe as determined by the vibration sensing means with the source vibrational level for shutting off the refrigeration means when the sensed vibration of the probe is below a predetermined level relative to the source vibrational level and turning on the refrigeration means when the sensed vibrational level returns to the source vibrational level and the control means periodically stopping the operation of the oscillating means for periodically stopping the vibrating of the probe so that ice can form thereon.

2. The sensor control as defined in claim 1, and the control means periodically stopping the operation of the oscillating means for predetermined time intervals.

3. The sensor control as defined in claim 1, and the control means synchronizing the operation of the oscillating means and the sensing by the vibrations sensing means.

4. The sensor control as defined in claim 1, and the control means or starting or stopping the operation of the refrigeration means only after a predetermined plurality of comparisons of the source vibration level and the sensed vibration indicate that such starting or stopping, respectively, should occur.

5. The sensor control as defined in claim 1, and the control means synchronizing the operation of the oscillating means and the sensing by the vibrations sensing means.

6. The sensor control as defined in claim 5, and the control means providing for starting or stopping the operation of the refrigeration means only after a predetermined plurality of comparisons of the source vibration level and the sensed vibration indicate that such starting or stopping, respectively, should occur.

* * * * *